(12) United States Patent
Coppe et al.

(10) Patent No.: US 8,432,171 B2
(45) Date of Patent: Apr. 30, 2013

(54) METHOD AND APPARATUS FOR MEASURING THE CONCENTRATION OF AN ANALYTE IN A SAMPLE FLUID

(75) Inventors: Thomas Coppe, Orbey (FR); Jean-Luc Henry, Colmar (FR); Michael Schoening, Juelich (DE)

(73) Assignee: Buerkert Werke GmbH, Ingelfingen (DE)

( * ) Notice: Subject to any disclaimer, the term of this patent is extended or adjusted under 35 U.S.C. 154(b) by 575 days.

(21) Appl. No.: 12/768,830

(22) Filed: Apr. 28, 2010

(65) Prior Publication Data

US 2010/0308843 A1 Dec. 9, 2010

(30) Foreign Application Priority Data

Apr. 29, 2009 (FR) ...................................... 09 52825

(51) Int. Cl.
*G01R 27/26* (2006.01)
(52) U.S. Cl.
USPC ........... 324/663; 324/660; 324/658; 324/668; 324/674; 324/675; 324/686; 73/304 R; 73/304 C; 442/82.01; 442/82.02; 204/433; 204/416; 257/253; 436/149; 436/150; 436/151; 436/163
(58) Field of Classification Search .................. 324/663, 324/660, 658, 668, 674, 675, 686; 73/304 R, 73/304 C; 422/82.01, 82.02; 204/433, 416; 257/253; 436/149, 150, 151, 163
See application file for complete search history.

(56) References Cited

U.S. PATENT DOCUMENTS

| | | | | |
|---|---|---|---|---|
| 3,753,092 A | * | 8/1973 | Ludlow et al. | 324/663 |
| 3,903,478 A | * | 9/1975 | Stuart et al. | 324/663 |
| 4,064,455 A | * | 12/1977 | Hopkins et al. | 324/663 |
| 4,301,401 A | * | 11/1981 | Roof et al. | 324/663 |
| 4,692,685 A | * | 9/1987 | Blaze | 324/692 |
| 4,896,099 A | * | 1/1990 | Suzuki | 324/667 |

(Continued)

FOREIGN PATENT DOCUMENTS

| | | |
|---|---|---|
| DE | 19708166 A1 | 9/1998 |
| EP | 0213825 A | 3/1987 |
| WO | 02052252 A | 7/2002 |

OTHER PUBLICATIONS

Katsube, "New Semiconductor Glucose Sensor Using Sputtered LaF3 Film", Solid-State Sensors and Actuators, 1991, pp. 78-81.*

(Continued)

*Primary Examiner* — Patrick Assouad
*Assistant Examiner* — Lamarr Brown
(74) *Attorney, Agent, or Firm* — Carlson, Gaskey & Olds, PC

(57) ABSTRACT

An analyte concentration, in a sample fluid, is determined by differential measurement. Two or more capacitive field effect sensors have an identical basic structure and are arranged in a shared measuring cell. One of the sensors forms a measuring sensor with an active transductor layer. Another sensor forms a reference sensor without an active transductor layer. The sensors are contacted with the sample fluid and the sensors, have an associated reference electrode, or have a shared reference electrode. A bias voltage composed of an electric DC voltage and a superimposed AC voltage is applied between each sensor and associated reference electrode(s) Capacitance changes due to the analyte are eliminated by controlling the bias voltage applied to the measuring sensor in a closed control loop. A measuring signal is obtained by calculating a difference between voltage values representative of DC voltage potentials applied to the measuring sensor and reference sensor, respectively.

15 Claims, 5 Drawing Sheets

U.S. PATENT DOCUMENTS

| | | | | |
|---|---|---|---|---|
| 5,168,240 A * | 12/1992 | Howe | ............................ | 324/690 |
| 5,262,731 A * | 11/1993 | Mizoguchi | .................... | 324/663 |
| 5,270,663 A * | 12/1993 | Sano et al. | ..................... | 324/676 |
| 5,282,381 A * | 2/1994 | Krone-Schmidt | ........... | 73/61.41 |
| 5,313,168 A * | 5/1994 | Ogawa | ........................... | 324/663 |
| 5,321,367 A * | 6/1994 | Koscica et al. | ............... | 324/663 |
| 5,365,783 A * | 11/1994 | Zweifel | ...................... | 73/304 C |
| 5,367,264 A * | 11/1994 | Brabetz | ......................... | 324/674 |
| 5,418,465 A * | 5/1995 | Seipler et al. | ................. | 324/663 |
| 6,132,893 A * | 10/2000 | Schoning et al. | ............ | 257/253 |
| 6,299,754 B1 * | 10/2001 | Mertens et al. | ............... | 205/263 |
| 6,321,101 B1 * | 11/2001 | Holmstrom | ................... | 600/345 |
| 6,464,940 B1 * | 10/2002 | Akioka et al. | ............. | 422/82.01 |
| 6,653,842 B2 * | 11/2003 | Mosley et al. | ................ | 324/446 |
| 7,335,336 B1 * | 2/2008 | Kim | ................................. | 422/88 |
| 7,820,029 B2 * | 10/2010 | Chou et al. | ................. | 205/787.5 |
| 2004/0104130 A1 * | 6/2004 | Mosley et al. | ................ | 205/787.5 |
| 2006/0147983 A1 * | 7/2006 | O'uchi | ............................... | 435/6 |
| 2007/0158190 A1 * | 7/2007 | Chou et al. | .................... | 204/416 |
| 2009/0011517 A1 * | 1/2009 | Hodges | ......................... | 436/139 |
| 2009/0041623 A1 * | 2/2009 | Lee et al. | ........................ | 422/63 |
| 2009/0145778 A1 * | 6/2009 | Allmendinger | ............... | 205/789 |
| 2009/0211924 A1 * | 8/2009 | West et al. | .................. | 205/787.5 |
| 2010/0180663 A1 * | 7/2010 | Sun | ................................ | 73/1.02 |
| 2010/0289505 A1 * | 11/2010 | Zhang | ........................... | 324/663 |
| 2010/0301398 A1 * | 12/2010 | Rothberg et al. | ............. | 257/253 |
| 2010/0321038 A1 * | 12/2010 | Dommaschk et al. | ........ | 324/658 |
| 2011/0031983 A1 * | 2/2011 | David et al. | ................... | 324/663 |
| 2011/0298481 A1 * | 12/2011 | Mayer et al. | .................. | 324/686 |
| 2012/0123738 A1 * | 5/2012 | Dorr et al. | ..................... | 702/184 |
| 2012/0166095 A1 * | 6/2012 | Potyrailo et al. | ................ | 702/23 |
| 2012/0235784 A1 * | 9/2012 | Teterwak et al. | .............. | 340/5.6 |
| 2012/0261274 A1 * | 10/2012 | Rearick et al. | ................ | 205/789 |

OTHER PUBLICATIONS

European Search Report dated Aug. 13, 2010.

Arjang Hassibi, et al., "A Programmable 0.18-CMOS Electrochemical Sensor Microarray for Biomolecular Detection," IEEE Sensors Journal, Dec. 1, 2006.

Poghossian, A., et al., "An ISFET-based Penicillin Sensor with High Sensitivity, Low Detection Limit and Long Lifetime," Sensors and Actuators, Jun. 1, 2001.

Poghossian, A., et al., "(Bio-)Chemical and Physical Microsensor Arrays Using an Identical Transducer Principle," Electrochimica Acta, Elsevier Science Publishers, Sep. 1, 2001.

Poghossian, A; Schoning, MJ, "Detecting Both Physical and (Bio-)Chemical Parameters by Means of ISFET Devices," Electroanalysis, Sep. 28, 2004.

French Search Report, dated Jan. 19, 2001.

Schoning, M. J., et al.: "A Novel Silicon-Based Sensor Array With Capacitive EIS Structures", Apr. 30, 1998.

Poghossian, A., et al.: "Cross-Sensitivity of a Capacitive Penicillin Sensor Combined With a Diffusion Barrier," Aug. 25, 2000.

Thust, M., et al.: "A Long-Term Stable Penicillin-Sensitive Potentiometric Biosensor With Enzyme Immobilized by Heterobifunctional Cross-Linking," Apr. 19, 1996.

* cited by examiner

METHOD AND APPARATUS FOR MEASURING THE CONCENTRATION OF AN ANALYTE IN A SAMPLE FLUID

RELATED APPLICATION

This application claims priority to French Application No. 09 52825, which was filed 29 Apr. 2009.

FIELD OF THE INVENTION

The invention relates to a method of measuring the concentration of an analyte in a sample fluid. It further relates to an apparatus for carrying out the method.

BACKGROUND

Semiconductor-based sensors which use capacitive measuring principles are known. They are used in the field of chemo- and biosensors. Sensors which make use of the selectivity of enzymes, for example, are referred to as biosensors. Biosensors in silicon technology in which an enzyme is fixed on the surface of the sensor are already known (DE 44 36 001 C2).

In one group of sensors, a chemical reaction takes place at the sensor which is selective for an ion or molecule and in which a change in pH value occurs at the same time. Examples of applications include the determination of heavy metals and pesticides in waste water, penicillin determination, and DNA analysis.

These sensors have in common that they are structured as pH sensors which are equipped with an additional sensitive layer for the analyte to be determined, the underlying pH-sensitive layer continuing to be active. This sensor principle results in a plurality of measurements having to be carried out in succession to be able to indicate the concentration of an analyte since the sensor detects both the pH value of a sample solution and the additional change in pH value resulting from the reaction of the analyte present in the sample solution with the second, sensitive layer.

SUMMARY

The invention allows an analyte concentration to be directly determined by differential measurement.

In one aspect of the invention a method of measuring a concentration of an analyte in a sample liquid or in a sample gas is proposed. At least two capacitive field effect sensors configured in semiconductor technology and having an identical basic structure are arranged in a shared measuring cell. One of the sensors forms a measuring sensor with an active transductor layer. Another sensor forms a reference sensor without an active transductor layer. The sensors either each have an associated reference electrode, or have a shared reference electrode. In accordance with the method, the sensors are simultaneously contacted with the sample liquid or sample gas. A bias voltage composed of an electric DC voltage and a superimposed AC voltage is applied between each sensor and the associated reference electrodes or the shared reference electrode. The reference electrode(s) is (are) simultaneously contacted by the sample liquid or gas. Any change in capacitance due to the analyte is then eliminated by controlling the bias voltage applied to the measuring sensor in a closed control loop. A measuring signal is obtained by calculating a difference between voltage values that are representative of the DC voltage potentials applied to the measuring sensor and to the reference sensor, respectively.

While the invention will be mainly described with respect to a penicillin sensor, it is applicable to any sensor based on the principle of a sensor reaction and a simultaneous change in pH value.

In a specific embodiment, an enzyme is fixed to a pH sensor, in particular having a silicon nitride or tantalum pentoxide surface or some other pH-sensitive surface, the enzyme reacting selectively with penicillin present in a sample to be measured, to form penicillic acid while releasing $H^+$ ions. To determine the penicillin concentration, a differential measurement is now carried out in the measuring apparatus according to the invention. This structure allows the penicillin concentration to be determined directly. It is thus no longer necessary to carry out successive measurements, as is required in the prior art.

Two sensors are simultaneously in contact with the sample liquid to be analyzed or the sample gas to be analyzed. A first pH sensor, preferably in the form of an EIS structure, establishes the pH value of the sample liquid to be determined. A second sensor, the biosensor, has a structure identical with that of the first sensor, a pH-active layer being additionally followed by the penicillin-sensitive, enzyme-based structure. Any penicillin present in the sample liquid will selectively become attached to the penicillin-sensitive structure, the penicillin reacting to form penicillic acid and $H^+$ ions being released. The latter are detected by the second sensor in addition to the $H^+$ ions that correspond to the original pH value of the sample liquid. Using an electronic evaluation unit, the $H^+$ ion concentration which is solely attributable to the enzymatic reaction and which corresponds to the penicillin concentration is determined from the measuring signals of the two sensors by forming the difference.

The possible miniaturization of the measuring apparatus described is of particular advantage both with respect to the fluidic components and the electronic measuring and evaluating device together in a compact structural unit for industrial applications.

To increase the service life of the sensors, it is especially expedient to contact the sensors alternately with the sample liquid and a buffer solution for neutralization using a spraying process.

These and other features of the present invention can be best understood from the following specification and drawings, the following of which is a brief description.

BRIEF DESCRIPTION OF THE DRAWINGS

Further features and advantages will become apparent from the description below, given with reference to the accompanying drawings, in which.

DETAILED DESCRIPTION

Figure 1:
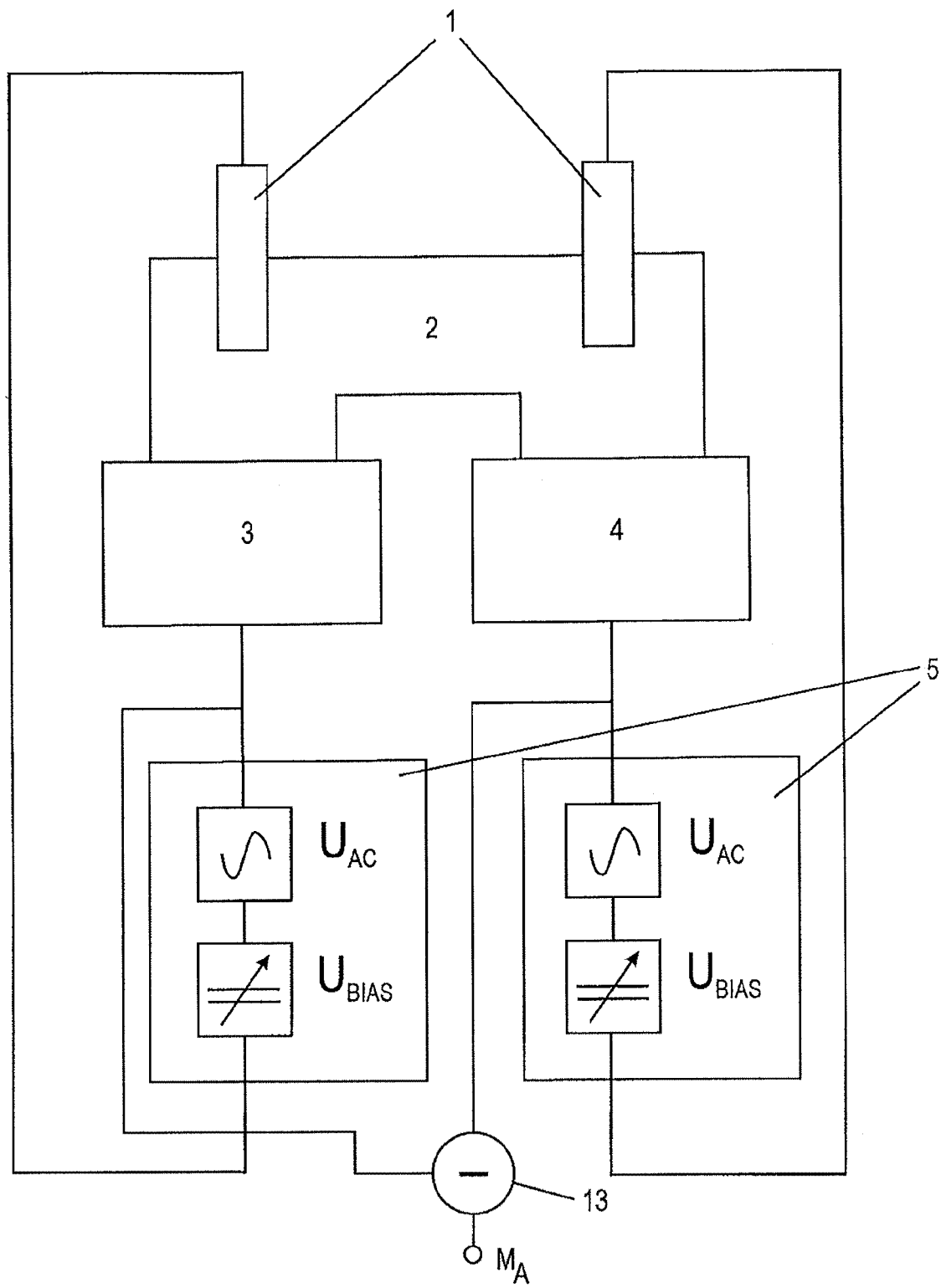
FIG. 1 shows a first embodiment of a sensor arrangement with two sensors.

FIG. 1 schematically shows a capacitive sensor arrangement according to a first embodiment of the invention.

A pH sensor 3 and a penicillin-sensitive biosensor 4 each have a contacting surface exposed to an analyte 2. Each sensor 3, 4 has an associated reference electrode 1 (e.g., Ag/AgCl) which dips into the analyte 2, preferably an aqueous sample liquid, thereby contacting one side of the sensors 3 and 4. Optionally, additional electrodes (such as platinum wire) may be used, which may be advantageous to ensure the continuity of the measurement. The rear sides of the sensors have contact pads to which two separate measuring circuits 5 are connected.

Both measuring circuits 5 for capacitance measurement are structured in the same manner, as already described in DE 19708166. Each contains a controllable DC voltage source connected in series with an AC voltage source. The measuring principle is based on using the AC voltage portion $U_{AC}$ to determine the capacitance of the sensor and controlling the DC voltage $U_{BIAS}$ so as to compensate for the change in capacitance caused by the presence of the analyte (i.e. the additionally released ions). The DC voltage potential applied to the sensor then corresponds to a measured value determined in the respective measuring circuit 5. Proceeding from the two measured values, the electronic measuring device containing both measuring circuits 5 then forms the measuring signal $M_A$ using a subtracting circuit 13, with the measuring signal $M_A$ directly indicating the concentration of the analyte. In the example chosen, the difference resulting from the two $H^+$ ion concentrations on the biosensor 4 and on the pH sensor 3 corresponds to the penicillin concentration in the sample liquid.

Figure 2:
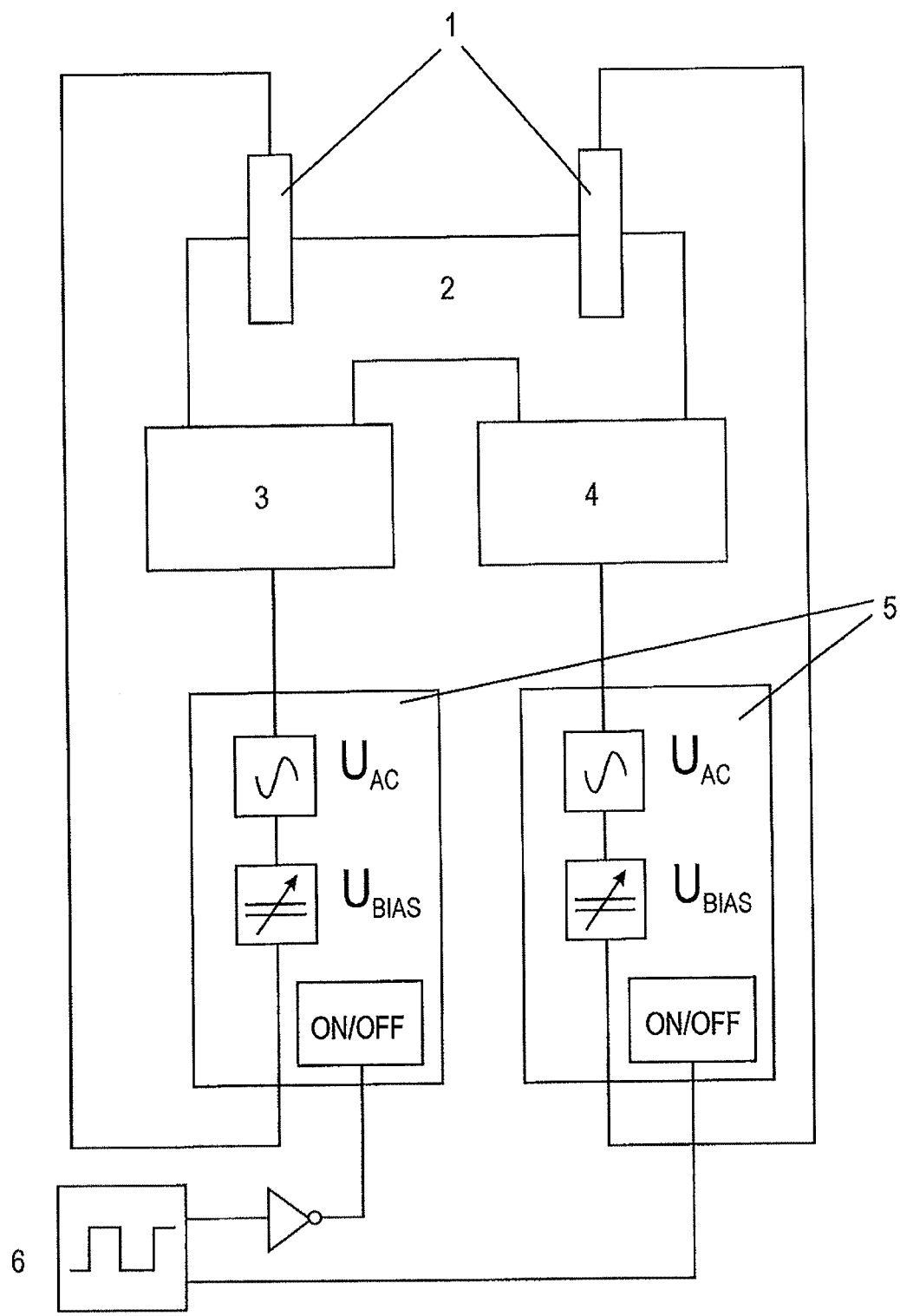
FIG. 2 shows a second, synchronized embodiment corresponding to FIG. 1.

FIG. 2 depicts an optimized embodiment, which additionally allows a synchronization by using a synchronizer 6. The two measuring circuits 5 are alternatingly activated and deactivated by the synchronizer 6.

Figure 3:
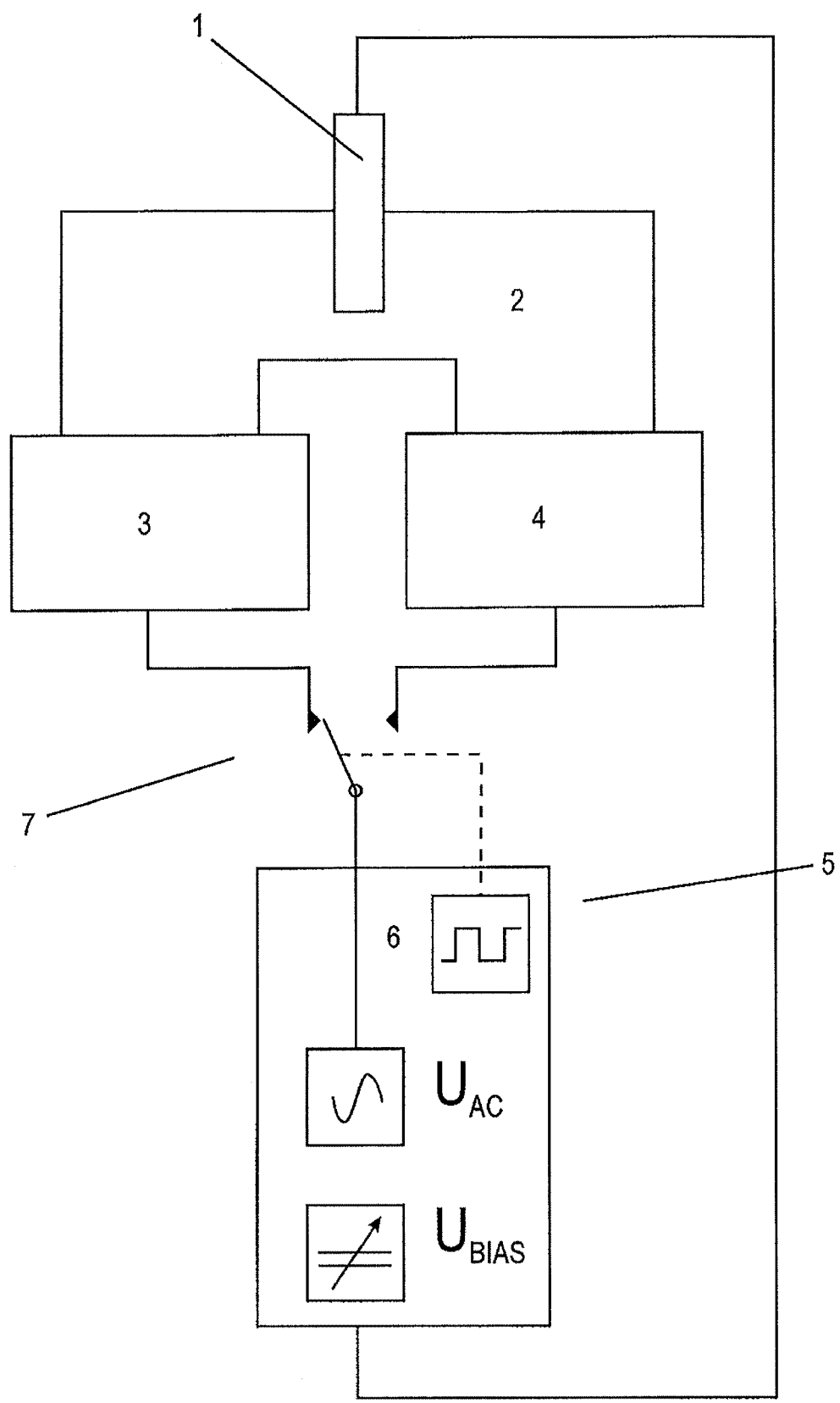
FIG. 3 shows a third embodiment of a sensor arrangement with two sensors.

FIG. 3 shows a further embodiment of the invention, which constitutes a simplification of the embodiments according to FIGS. 1 and 2. One single reference electrode 1 dips into the analyte 2 and is electrically connected to a measuring circuit 5 which is additionally connected alternately (as controlled by a clock signal) to the sensor rear side contact pad either of the pH sensor 3 or of the bio sensor 4 by a switch 7. For calculating the difference, the measured values obtained for the sensors are stored temporarily.

Figure 4:
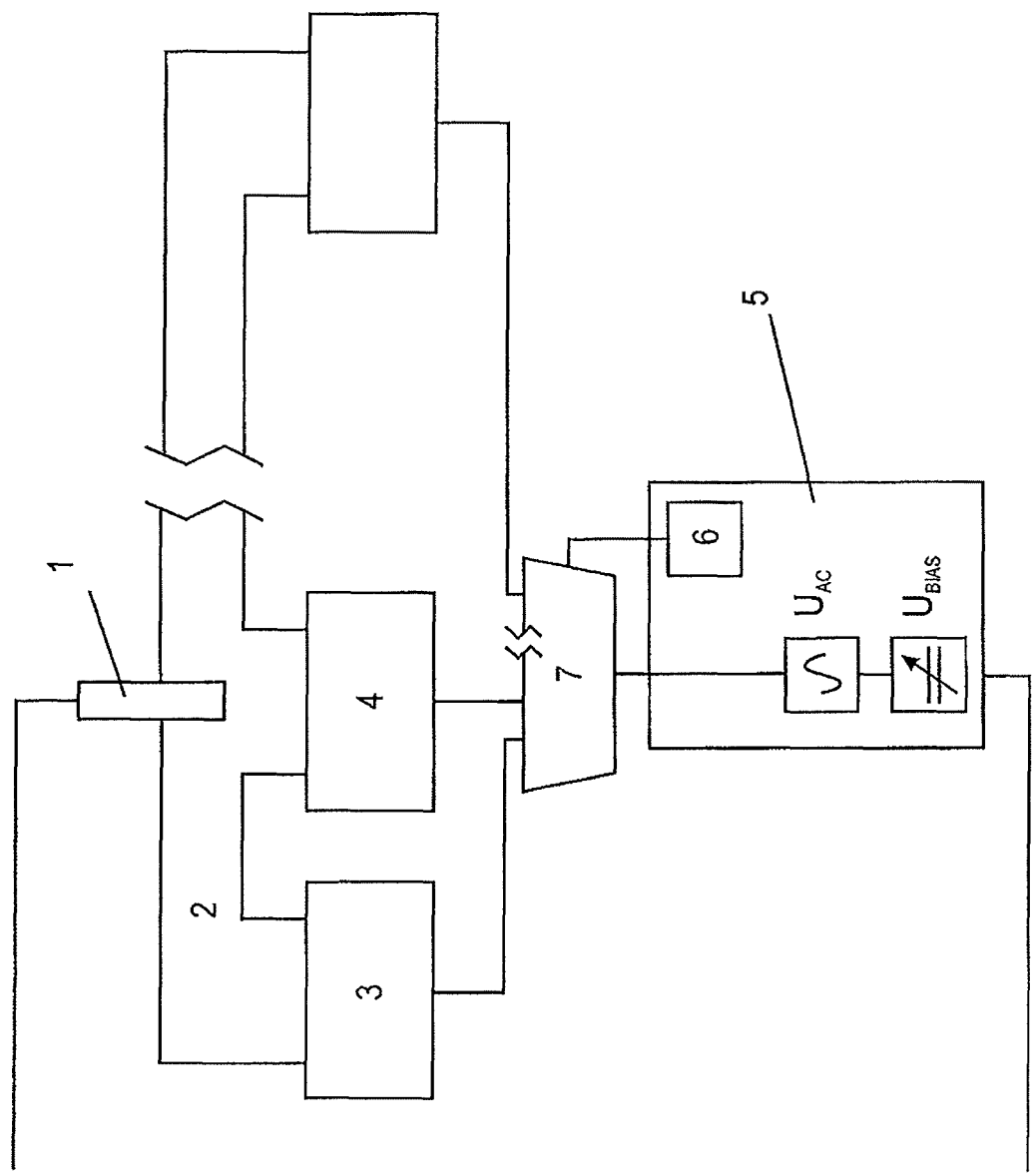
FIG. 4 shows an embodiment with any desired number of sensors.

As illustrated in FIG. 4, the measuring principle and the evaluation are extendable to any number of sensors connected in parallel, the difference being determined to the pH sensor in each case.

Figure 5:
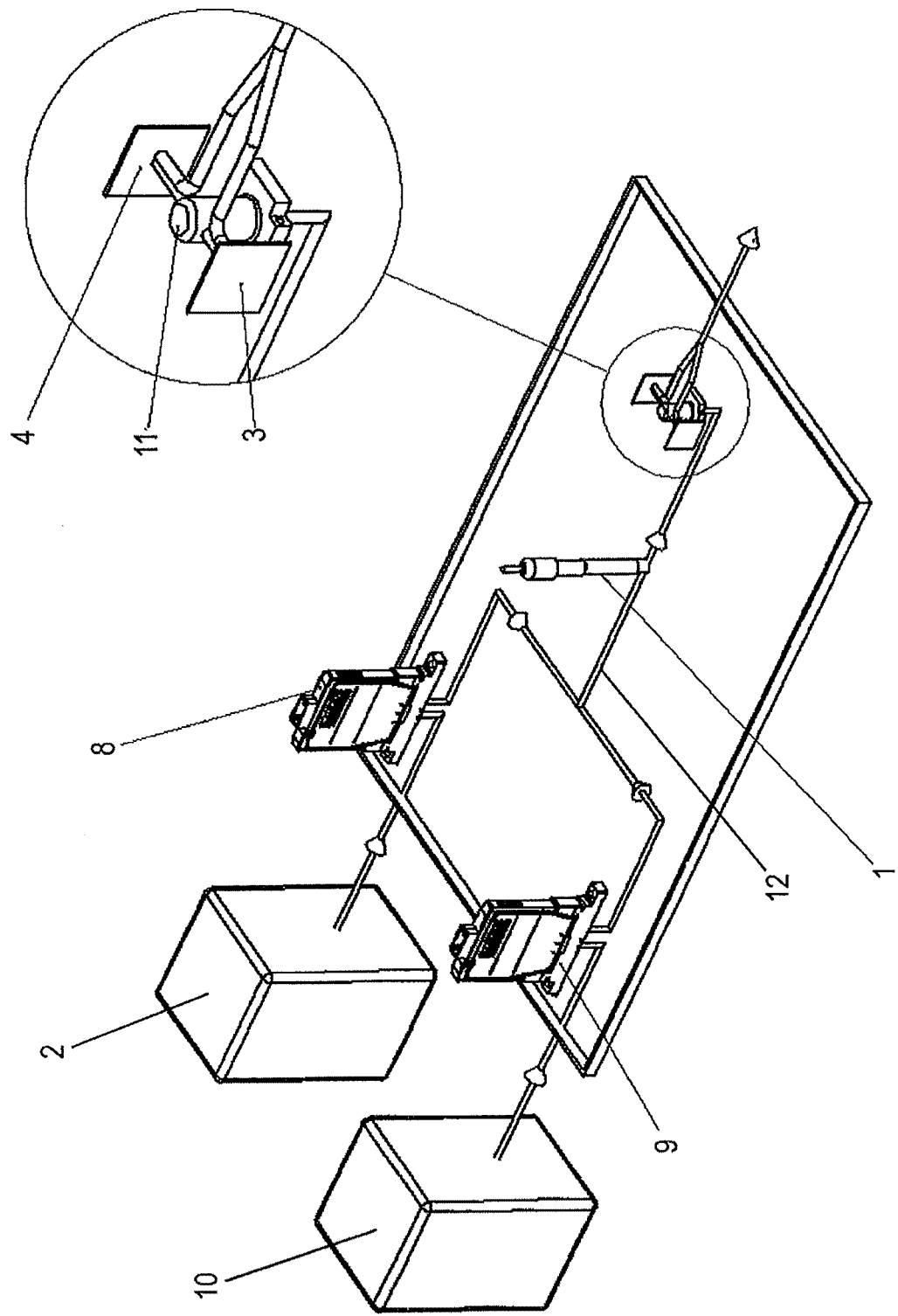
FIG. 5 shows the fluidic implementation of the embodiment of a sensor arrangement with two sensors.

A fluidic implementation of the embodiment of a sensor arrangement including two sensors is shown in FIG. 5.

Sample liquid 2 from a sample container is conveyed in a fluid channel 12 via a first valve 8 to a distributor nozzle 11, which sprays a respective sensor side of each of the first sensor 3 (pH sensor) and the second sensor 4 (penicillin sensitive biosensor) with sample liquid. A reference electrode 1 dips into the fluid channel 12. As described above, the sensor rear sides and the reference electrode 1 are in electrical connection with the electronic measuring device (not illustrated in FIG. 5).

A container with a buffer solution 10 supplies a second valve 9 with buffer solution, which is conveyed into the fluid channel 12 following one or more measurements and reaches the sensors 3, 4 via the distributor nozzle 11. This rinsing process downstream of the measurement provides for a neutralization of the sensor surfaces and considerably extends the service life of the sensors.

The two valves 8 and 9 are both closed in the rest mode; in the measuring mode, valve 8 is open and valve 9 is closed, whereas in the purging mode, valve 8 is closed and valve 9 is open.

Although an embodiment of this invention has been disclosed, a worker of ordinary skill in this art would recognize that certain modifications would come within the scope of this invention. For that reason, the following claims should be studied to determine the true scope and content of this invention.

What is claimed is:

1. A method of measuring a concentration of an analyte contained in a sample fluid, wherein at least two capacitive field effect sensors configured in semiconductor technology and having an identical basic structure with a reference electrode are arranged in a shared measuring cell, one of said at least two capacitive field effect sensors forming a measuring sensor with an active transductor layer and another one of said at least two capacitive field effect sensors forming a reference sensor without an active transductor layer, said method comprising the steps of:

simultaneously contacting said at least two capacitive field effect sensors with said sample fluid;

applying a bias voltage which is composed of an electric DC voltage and a superimposed AC voltage between each capacitive field effect sensor and the reference electrode, said reference electrode being simultaneously contacted by said sample fluid;

eliminating any change in capacitance due to the analyte in the sample fluid by controlling said bias voltage applied to said measuring sensor in a closed control loop; and obtaining a measuring signal by calculating a difference between voltage values that are representative of DC voltage potentials applied to said measuring sensor and to said reference sensor, respectively.

2. The method as claimed in claim 1, wherein each capacitive field effect sensor includes an associated reference electrode and an associated electronic measuring circuit for applying said controlled bias voltage with said superimposed AC voltage.

3. The method as claimed in claim 2, wherein said capacitive field effect sensors are operated simultaneously.

4. The method as claimed in claim 2, wherein said capacitive field effect sensors are operated alternately with only one electronic measuring circuit which is switched over between said capacitive field effect sensors.

5. The method as claimed in claim 1, wherein said capacitive field effect sensors have a shared reference electrode and a shared electronic measuring circuit and said controlled bias voltage with said superimposed AC voltage is alternately applied between said shared electrode and one of said capacitive field effect sensors.

6. The method as claimed in claim 5, wherein one reference sensor and a plurality of sensors having different transductor layers are arranged in said measuring cell.

7. The method as claimed in claim 1, wherein said measuring cell is alternately exposed to said sample liquid containing said analyte and to a buffer solution.

8. The method as claimed in claim 1, wherein said capacitive field effect sensors measure one of pH values and ion concentrations.

9. An apparatus for measuring a concentration of an analyte contained in a sample fluid comprising:

a shared measuring cell in which at least two capacitive field effect sensors are arranged which are configured in semiconductor technology and have an identical basic structure with a reference electrode, one of said capacitive field effect sensors forming a measuring sensor with an active transductor layer and another one of said capacitive field effect sensors forming a reference sensor without an active transductor layer; and an electronic measuring device including a DC voltage source connected in series with an AC voltage source, the DC voltage source being controllable in a closed loop to eliminate any changes in capacitance of said measuring sensor due said analyte and to derive a measuring signal by calculating a difference between voltage values that are representative of potentials of said DC voltage applied to said measuring sensor and to said reference sensor, respectively.

10. The apparatus as claimed in claim 9, wherein each capacitive field effect sensor has an associated reference electrode and an associated electronic measuring circuit.

11. The apparatus as claimed in claim 9, wherein said capacitive field effect sensors have a shared reference electrode, which may be formed by one of said capacitive field effect sensors.

12. The apparatus as claimed in claim 11, wherein said capacitive field effect sensors have a shared electronic measuring circuit that is adapted to be switched over between said capacitive field effect sensors.

13. The apparatus as claimed in claim 9, wherein said capacitive field effect sensors are one of pH-sensitive and ion-sensitive.

14. The apparatus as claimed in claim 9, wherein said active transductor layer includes a fixed enzyme.

15. The apparatus as claimed in claim 9, wherein said measuring cell is adapted to be exposed to said sample liquid and to a buffer solution by alternately controlled valves.

* * * * *